(12) United States Patent
Dahl (10) Patent No.: US 7,883,849 B1
(45) Date of Patent: Feb. 8, 2011

(54) METHOD FOR AMPLIFYING SPECIFIC NUCLEIC ACIDS IN PARALLEL

(75) Inventor: Fredrik Dahl, Palo Alto, CA (US)

(73) Assignee: Olink AB, Uppsala (SE)

( * ) Notice: Subject to any disclaimer, the term of this patent is extended or adjusted under 35 U.S.C. 154(b) by 526 days.

(21) Appl. No.: 11/596,972

(22) PCT Filed: Mar. 31, 2005

(86) PCT No.: PCT/SE2005/000464

§ 371 (c)(1),
(2), (4) Date: Nov. 5, 2007

(87) PCT Pub. No.: WO2005/111236

PCT Pub. Date: Nov. 24, 2005

(30) Foreign Application Priority Data

May 18, 2004 (SE) .................................. 0401270

(51) Int. Cl.
*C12Q 1/68* (2006.01)
(52) U.S. Cl. .......................................................... 435/6
(58) Field of Classification Search ....................... None
See application file for complete search history.

(56) References Cited

U.S. PATENT DOCUMENTS

| 6,274,320 | B1 | 8/2001 | Rothberg et al. | |
|---|---|---|---|---|
| 6,361,947 | B1 * | 3/2002 | Dong et al. | ........... 435/6 |
| 6,706,476 | B1 | 3/2004 | Thirstrup et al. | |
| 2005/0287526 | A1 | 12/2005 | Landegren et al. | |

FOREIGN PATENT DOCUMENTS

| EP | 1350853 A1 | 10/2003 |
|---|---|---|
| WO | 96/41012 A1 | 12/1996 |
| WO | 98/40518 A3 | 9/1998 |
| WO | 9949079 A1 | 9/1999 |
| WO | 03/012119 A2 | 2/2003 |
| WO | 03/044229 A1 | 5/2003 |

OTHER PUBLICATIONS

Lyamichev et al., Structure-specific endonucleolytic cleavage of nucleic acids by eubacterial DNA polymerases, Science, 260:778-783 (May 7, 1993).
Lizardi et al., Mutation detection and single-molecule counting using isothermal rolling-circle amplification, Nature Genetics, 19:225-232 (Jul. 1998).
Kennedy et al., Large-scale genotyping of complex DNA, Nature Biotechnology, 21(10)1233-1237 (Oct. 2003).
Landegren, Molecular mechanics of nucleic acid sequence amplification, Trends Genet., 9(6)199-204 (1993).
Zhang et al., Whole genome amplification from a single cell: Implications for genetic analysis, Proc. Natl. Acad. Sci. USA, 89:5847-5851 (Jul. 1992).
Cheung et al., Whole genome amplification using a degenerate oligonucleotide primer allows hundreds of genotypes to be performed on less than one nanogram of genomic DNA, Proc. Natl. Acad. Sci. USA, 93:14676-14679 (Dec. 1996).
Broude et al., Multiplex allele-specific target amplification based on PCR suppression, Proc. Natl. Acad. Sci. USA, 98(1)206-211 (Jan. 2, 2001).
Callow et al., Selective DNA amplification from complex genomes using universal double-sided adapters, Nucleic Acids Research, 32(2e21) (2004).
Schouten et al., Relative quantification of 40 nucleic acid sequences by multiplex ligation-dependent probe amplification, Nucleic Acids Research, 30(12e57) (2002).

* cited by examiner

*Primary Examiner*—Christopher M. Babic
(74) *Attorney, Agent, or Firm*—Browdy and Neimark, PLLC (57) ABSTRACT

A method for amplifying a plurality of target sequences that minimizes amplification artefacts is provided. A sample of interest is fragmented into fragments, where each fragment that includes a target sequence has at least one defined end sequence. Selector constructs, all comprising a primer pair motif and each individual selector comprising one or two protruding ends complementary to the defined end sequences of the fragments containing the target sequences, are brought in contact with the fragments. After ligation, the selected target sequences are amplified in parallel using a primer-pair specific for the primer-pair motif common to the selectors.

14 Claims, 5 Drawing Sheets

METHOD FOR AMPLIFYING SPECIFIC NUCLEIC ACIDS IN PARALLEL

FIELD OF THE INVENTION

This invention relates to methods for amplifying a plurality of specific nucleic acids in parallel by PCR without the amplification artifacts usually found in such methods. The invention also concerns analysis of the amplified products.

BACKGROUND

PCR is probably the most important contribution among techniques that have revolutionized the uncovering of the human genome. Today, the vast majority of methods for identifying sequences in the human genome involve target sequence amplification through PCR.

A crucial problem with PCR is that when large numbers of specific DNA sequences are simultaneously amplified in the same reaction tube, then undesired amplification products often arise. The undesired amplification products in multiplex PCR are associated with, and increased in relation to, the number of the added primer-pairs. Even with careful attention paid to the design of the primers, PCR is usually limited to 10 simultaneous amplification reactions before false amplification products are formed. Therefore, in research projects that comprise identification and analysis of many nucleic acids sequences, a large number of separate PCRs must be performed.

Today, a PCR generally takes about two hours to perform and requires a defined amount of target material. In investigations where many PCRs must be performed, the projects often prove time consuming, expensive, and require a large collection of target DNA.

Different methods to overcome the problems associated with conventional multiplex PCR have been developed, but none with full success.

PCT publication WO 96/41012 discloses a method for multiplex PCR that entails two rounds of amplification and that uses primer pairs comprising template-specific sequences at their respective 3' ends and universal primer sequences at their respective 5' ends. The first round of amplification uses the specific primer sequences and the second amplification uses the universal primer sequences.

DOP-PCR (degenerate oligonucleotide-primed PCR) is a form of PCR which is designed to produce several different products through use of degenerated primers (Zhang, et al. Proc. Natl. Acad. Sci. USA 89, 5847-5851 (1992); Cheung and Nelson Proc. Natl. Acad. Sci. USA 93, 14676-14679 (1996)). The method is mainly used for "whole genome amplification" and lacks the means for selectively choosing a number of targets to be amplified in parallel.

Also, a number of DNA amplification methods that use so called adaptor-ligation PCR have been developed in different formats. Broude, et al., Proc. Natl. Acad. Sci. USA 98, 206-211 (2001) presented an approach to use single specific primers for each target and a single common primer. Kennedy, et al. Nat Biotechnol 21, 1233-1237 (2003) presents a method for fragment selection and complexity reduction through adaptor ligation on a digested whole genome sample. The ligation of adaptors to digested sample is then followed by a PCR that is set to amplified fragments of a certain size. All these methods have in common that they cannot amplify many specific fragments in parallel without amplifying a large collection of undesired DNA targets at the same time. Callow, et al. Nucleic Acids Res 32, E21 (2003) present a technique to use adaptor-ligation PCR together with a specific selection of targets using rounds of Type IIs restriction enzyme cleavage. This method suffers from the lack of ability to amplify a large set of specific targets in parallel, and therefore remains limited in its application.

The method uses Type IIs restriction enzymes that produce 4-base, 5'-overhang of digested genomic DNA to fragment the genome into 32768 variants of overhangs (non-directional). To avoid hybridization and ligation of double-sided adaptors to itself, all 16 palindrome 4-base combinations must be avoided resulting in a design success-rate of 88% for any given Type IIs restriction enzyme. To avoid hybridization and ligation of one double-sided adaptor to another no 4-base overhang combination complementary to another adaptor's overhang can be used. This limitation results in an increasing difficulty of finding suitable adaptors for increasing number of targets to be amplified.

As an example for one round of selection; when a random set of 10 fragments from the human DNA is chosen to be amplified in parallel, the chance of finding all corresponding adaptors is only 50%. Or even worse, when a random set of 50 fragments is chosen to be amplified in parallel, there is almost no chance of finding the pool of corresponding adaptors ($2.2 \cdot 10^{-9}$%) that selects all 50 fragments. The limitation of using only 4-base combinations to select all fragments in a complex DNA sample such as the human genome results in that the method can not be used for parallel amplification of large sets of specific targets. The method can be used to amplify subsets of genomes or very few targets in parallel but lacks the freedom of action of amplify large sets of specific targets without producing unwanted DNA.

PCT publications WO 03/012119 and WO 03/044229 disclose methods to specifically circularize genomic fragments and amplify them with so called rolling circle amplification. These two publications do not disclose PCR amplification of the selected fragments and do not contain a description of the design of the selector.

Thus, there exists a need for methods that permit amplification of multiple specific DNA sequences in the same reaction without producing amplification artifacts.

SUMMARY OF THE INVENTION

The present invention fulfils these requirements and results in fewer amplification reactions and therefore use of less target material, by introducing a novel method of reducing undesired amplification products in multiplex DNA amplification reaction of large numbers of specific nucleic acid sequences. In another aspect, the present invention provides a method of selecting multiple desired nucleic acid sequences from a complex sample of DNA to be amplified in parallel.

The present invention is based on hybridization and ligation of target specific oligonucleotide construct, "selectors", to specific target nucleic acid sequences. The selectors all contain a common sequence that is a general primer-pair motif. All specifically ligated target sequences can therefore be amplified in multiplex manner using only one or a small number of primer-pairs.

The first aspect of the invention is the selector construct.

In a second aspect of the invention there is provided a method, defined in claim 1.

In the first step, the sample nucleic acid is cleaved at any predetermined site to generate fitting ends that can be connected to the selectors. This step is preferably made by adding one, or a pool of restriction enzyme(s) to the sample.

In the next step, if the nucleic acid is double stranded, the digested nucleic acid sample is denaturated to be single stranded.

In the next step, the selectors are hybridized and joined to respective target sequence ends.

In the last step the newly formed molecules (the selected targets joined with the corresponding selectors) are amplified simultaneously in the same reaction tube with one common primer-pair.

After the amplification reaction, the products can be analyzed using methods for nucleic acid analysis known in the art, such as DNA microarrays, gel-electrophoresis, or mass-spectrometry.

In a preferred embodiment of the invention, the nucleic acid sample is a DNA sample.

A third aspect of the invention concerns a kit of reagents for carrying out the method according to the invention.

A fourth aspect of the invention is a method of designing the selectors and selecting which restriction enzyme(s) to use in the method according to the invention.

BRIEF DESCRIPTION OF THE DRAWINGS

The accompanying drawings illustrate embodiments of the invention and, together with the description, serve to explain the invention:

FIG. 1 illustrates the first step of the procedure. Digestion of genomic DNA with one or a pool of restriction enzyme, results in fragments with defined ends. The digested fragments are denatured to single stranded DNA and added together with the designed selectors. Each of the selectors is composed of two oligonucleotides, a long and a short, which are hybridized to each other; one which contains one or two target specific ends and at least one primer motif, and a shorter one that contains at least one primer motif.

DETAILED DESCRIPTION OF THE INVENTION

In the following description of the method the amplification of the selector/target molecule is exemplified by PCR amplification but other amplification methods are equally possible. The invention disclosed herein advantageously improves the performance of nucleic acid amplification in parallel, particularly compared to methods in which many templates are amplified in parallel using a primer pair for each template to be amplified. These conventional multiplex PCR is known, by those of ordinary skills in the art, to produce amplification artifacts that hinder analysis of the desired amplified targets.

For the purposes of this invention, the following expressions are defined as follows:

"Selector construct", or "selector", is a target specific oligonucleotide construct. The selector herein refers to two partially hybridizing oligonucleotides; one long oligonucleotide that has one or two target specific ends and at least one primer motif, and one short complementary oligonucleotide that contains at least one primer motif. The long and short oligonucleotides can independently be DNA, RNA, PNA or any other synthetic nucleic acid derivative. Preferably, both oligonucleotides are DNA.

The term "primer motif" is a nucleic acid sequence that contains a segment that is suitable for primer hybridization in a PCR reaction. Such primer motifs are known in the art and any such motif could be used in the invention.

"Defined end sequence" is any 5'- or 3'-end sequence of a nucleic acid that is known to the person working with the nucleic acid. Typically, the defined end sequence is the result of treatment of the nucleic acid sample with at least one restriction enzyme, i.e. one restriction enzyme or a pool of restriction enzymes. Analogously, "defined internal sequence" is an internal sequence of a nucleic acid that is known to the person working with the nucleic acid.

A "target", "target sequence" or "target nucleic acid" is a subsequence that should be amplified from a sample. A nucleic acid sample could contain several target sequences. For example, the nucleic acid sample of Example 1 contains ninety-six target sequences, but a sample may contain several hundred, thousands or more target sequences.

Amplification "in parallel" means that a plurality of amplification reactions take place at the same time, and usually in the same reaction vessel. Multiplex PCR is one variant of amplification in parallel.

The first aspect of the invention is the selector construct itself.

Typically, the long oligonucleotide in the selector contains one or two target specific ends and at least one primer motif. Each target specific end is typically 5-50 nucleotides long, preferably 10-20 nucleotides, and the primer motif is typically 10-50 nucleotides long, preferably 30-40 nucleotides.

The short oligonucleotide in the selector is typically 10-50 nucleotides long, preferably 30-40 nucleotides and contains at least one primer motif, each. The short oligonucleotide is complementary to the primer motif in the long oligonucleotide.

The protruding ends of the selector are designed to specifically hybridize to a selected target nucleic acid. After hybridization, the selector and the target nucleic acid is covalently joined by ligation. Hybridization and ligation of many individually designed selectors to respectively specific target sequences can be made in parallel. If the selector is incompletely hybridized, that is, when the ends of the selectors do not hybridize correctly to the target nucleic acid, the ligation event will not take place, and the following PCR will not result in an amplification product.

The method according to the second aspect of the invention comprises cleaving a DNA sample to fragments that contains the sequences to be amplified and investigated. The sample DNA is preferably cleaved by addition of one, or a pool of, restriction enzyme(s) to generate defined end sequences that can be connected to the selectors. The digested DNA sample is then denatured to single stranded DNA and is now ready for selection by hybridization to the target specific ends of the selectors. This step can be performed in different ways; A)

Figure 1:
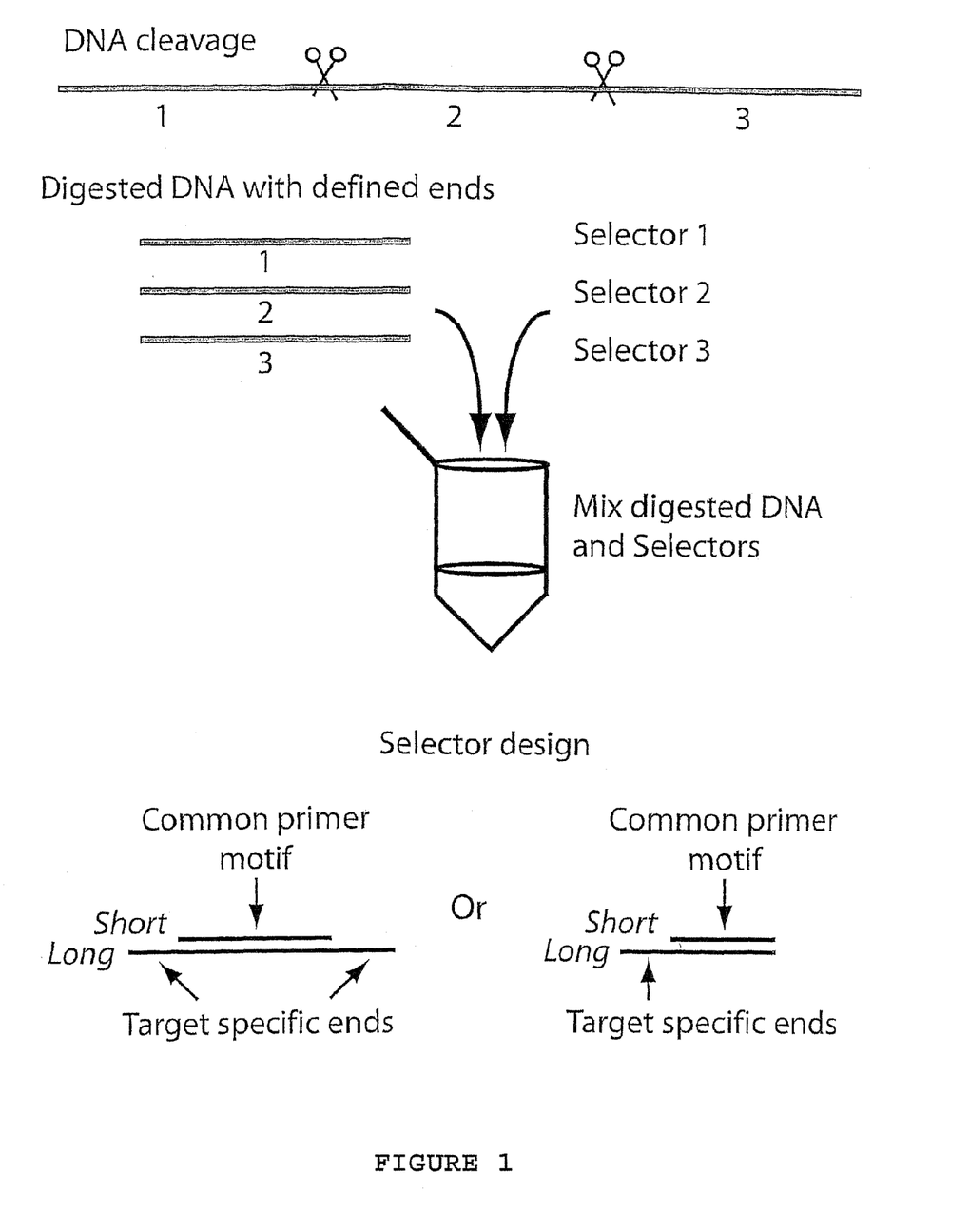
Figure 2:
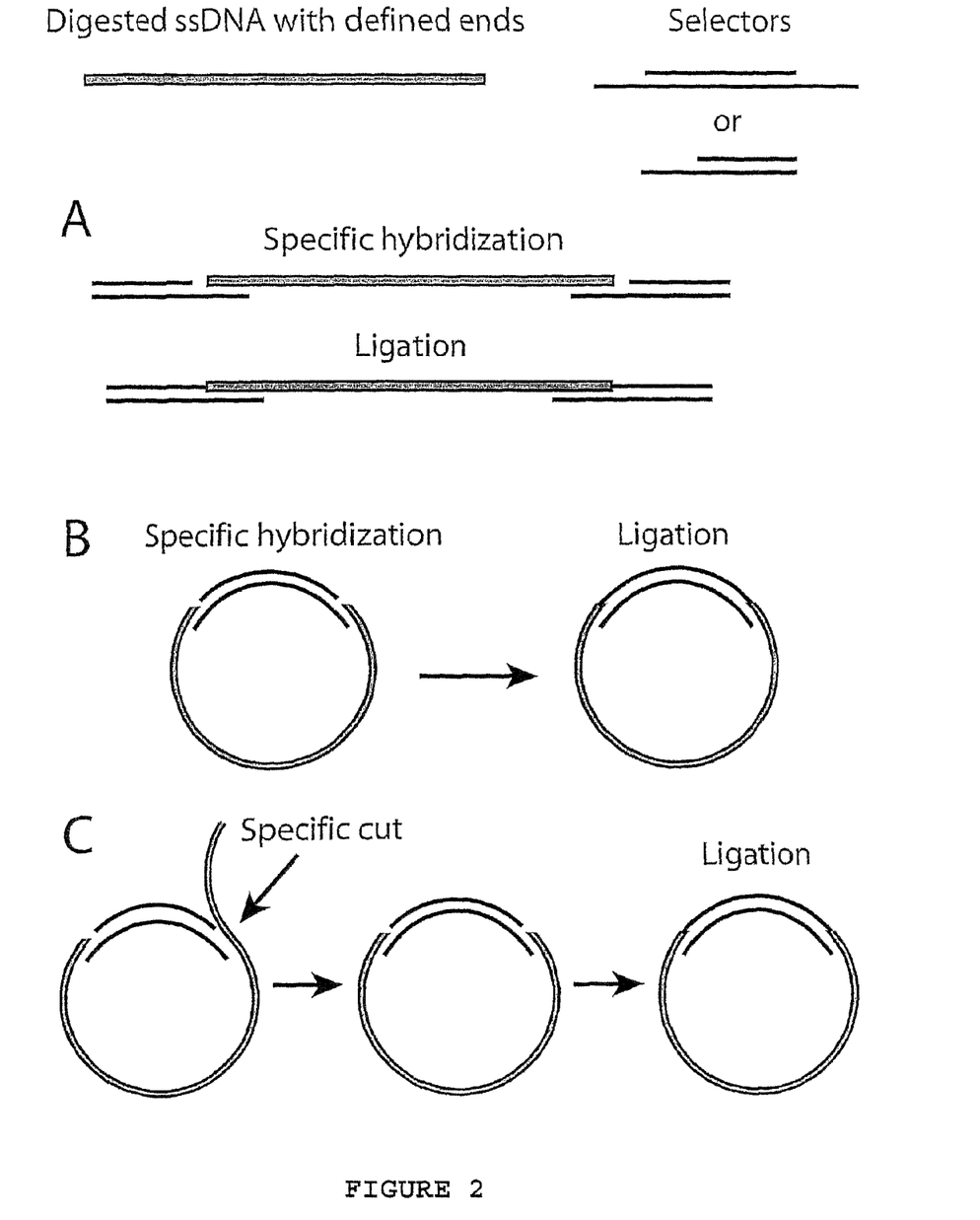
FIG. 2 the selectors are ligated to respective end of the selected digested single stranded DNA-targets (ssDNA). This process can be performed in different ways; A. Selectors are ligated to respective ends of a linear single stranded digested target. B. One selector can connect both ends of one selected single stranded target to form a circular DNA molecule. C. One end of the selector is connected to one end of the single stranded selected target, and the other end hybridizes to an internal sequence in the target. This structure is cleaved by an added enzyme with endonucleolytic activity, making both ends of the target suitable to be connected with the selector by ligation.

The selected single stranded targets can each be hybridized and joined to two selectors, one at each end of each target (FIG. 2A). B) The selected single stranded targets can be hybridized and joined by one selector each connecting both ends of each target, to form a circular molecule (FIG. 2B). C) One specific end of the selector can hybridize to the 3'-end of the target and the other specific end of the selector can hybridize to an internal sequence of the target. The protruding 5' arm of the target can be cleaved of by an endonucleolytic enzyme at the hybridization duplex position, according to Lymiachev et al., Science 260, 778-783 (1993). Both ends of the selector can now be connected to the selected single stranded target to form a closed circular molecule (FIG. 2C). With this procedure the 5' end of the target can be chosen without being limited by the presence of recognition sequences for restriction enzymes. The procedure also allows constructs containing only the sequence of interest and constructs with defined size. For some applications it may be desirable to generate amplified fragment of uniform length while for other application it may be advantageous to generate fragments of non-uniform length to use the length of the fragment for identification of the fragments or to ensure that all relevant sequence information from each fragment is included in the amplification product.

The aspect above is described with reference to DNA, but it may also be carried out on RNA, e.g. mRNA. The DNA can be cDNA, genomic DNA or DNA of any other origin.

Connection of selectors to selected single stranded targets is preferably made by enzymatic ligation.

When circular selector/target constructs are generated it is possible to use nucleolytic enzymes to remove remaining linear DNA fragment and thus reduce the risk for unspecific amplification products from these fragments.

Further in this aspect, the invention provides multiplex PCR of the selected targets. The selected targets now contain one or two selectors (depending on chosen selection procedure) that have the same primer-pair motif, which makes them suitable for multiplex PCR using only one general primer-pair. This result in that only targets ligated to selectors are amplified, and that all targets ligated to selectors can be amplified in parallel without producing any amplification artifacts that is related to conventional multiplex PCR with several primer-pairs.

In one embodiment of this aspect, the selectors may be divided into several subsets, wherein each set has a unique primer-pair motif. Different primer-pairs may thus be used to amplify different target sequences.

Although PCR is the presently preferred amplification method, it is of course possible to use other amplification methods. These methods include e.g. HRCA (Hyperbranched rolling-circle-amplification) described by Lizardi et al. (Lizardi, P. M., Huang, X., Zhu, Z., Bray-Ward, P., Thomas, D. C. & Ward, D. C. (1998) *Nat Genet* 19, 225-32.), NASBA and SDA (Landegren, U. (1993) *Trends Genet* 9, 199-204).

Due to the various selection methods, it is easy to construct the selected targets in optional size. This property makes the method easy to adjust for different nucleic acid analysis procedures.

The analysis of the amplification products may be carried out with any method known in the art, e.g. gel-electrophoresis, microarray technology, hybridization assays, sequencing by synthesis, liquid chromatography, mass spectrometry or the like.

The method can e.g. be used for the purposes of analyzing genetic variability, identification of micro-organisms, expression analysis, sequencing of genomes or DNA copy number measurements.

For example, the selector-concept shows promising qualities for the diagnostic field. Schouten et al. *Nucleic Acids Res*, 30, e57 (2002) have developed the multiplexed ligation-dependent probe amplification method (MLPA), for detecting copy number changes in specific chromosomal sequences as for example chromosome deletions and duplications. The quantitative analysis is based on separating a set of PCR-amplified size-tagged MLPA probes by gel electrophoresis.

Instead of separating a set of MLPA probes, differently sized PCR products created from selector reactions can be separated using the same type of size separating instruments. Selectors can be designed to select the disease causing targets, amplify the targets in parallel followed by a quantitative analysis of the amplified product.

Due to the multiplex character of the reaction, the amplified products are also well suited for highly parallel analysis such as for large scale sequencing, genotyping, haplotyping, or comparative genome hybridization. The massively parallel sequencing by synthesis methods developed by 454 Life Science is one example of a large scale sequencing system that could benefit from the selector technology.

The third aspect of the invention is a kit comprising reagents for carrying out the multiplex PCR according to the invention. The kit should at least comprise the selectors for the targets to be amplified, either separated or mixed together. The selectors should be designed to select the desired targets when used with a certain restriction enzyme or pool of restriction enzymes. The kit may additionally comprise the(se) restriction enzyme(s).

Furthermore, the kit may comprise additional reagents needed to carry out the method according to the invention as described above, such as buffers, ligase(s) and/or polymerase(s), utensils such as test tubes, and instructions on how to use the kit in the method according to the second aspect of the invention.

The fourth aspect of the invention is a method of designing the selectors and selecting the restriction enzymes. Preferably, the sequence of the nucleic acid sample is known. The method for designing the selectors and selecting the restriction enzymes comprise the steps:

i) Finding, in a nucleic acid sequence, restriction sites that flank target sequences to be amplified, ii) Selecting restriction enzymes that cleave the sample sequence in such a way that, either
   a) the single stranded fragments containing target sequences have two defined end sequences not found in any fragment not containing a target sequence, or
   b) the single stranded fragments containing target sequences have one defined end sequence and one defined internal sequence not found in any fragment not containing a target sequence
   and iii) Designing selectors for each fragment containing a target sequence so that each selector comprises:
   a) one defined end sequence complementary to one defined end sequence of the fragment containing a target sequence;
   b) a primer motif; and
   c) if applicable, one more defined end sequence complementary either to the other defined end sequence of the fragment containing a target sequence or to the defined internal sequence of that fragment.

Preferably, this aspect of the invention is implemented in a computer program. Thus, one embodiment of this aspect of the invention is a computer program product comprising the software code means for performing a method of designing selectors and/or selecting restriction enzymes for use in a certain specific embodiment of the method according to the first aspect of this invention.

Example 1

The following example illustrates the procedure of the method according to the invention. The example is offered by way of illustration and not by way of limitation.

Figure 3:
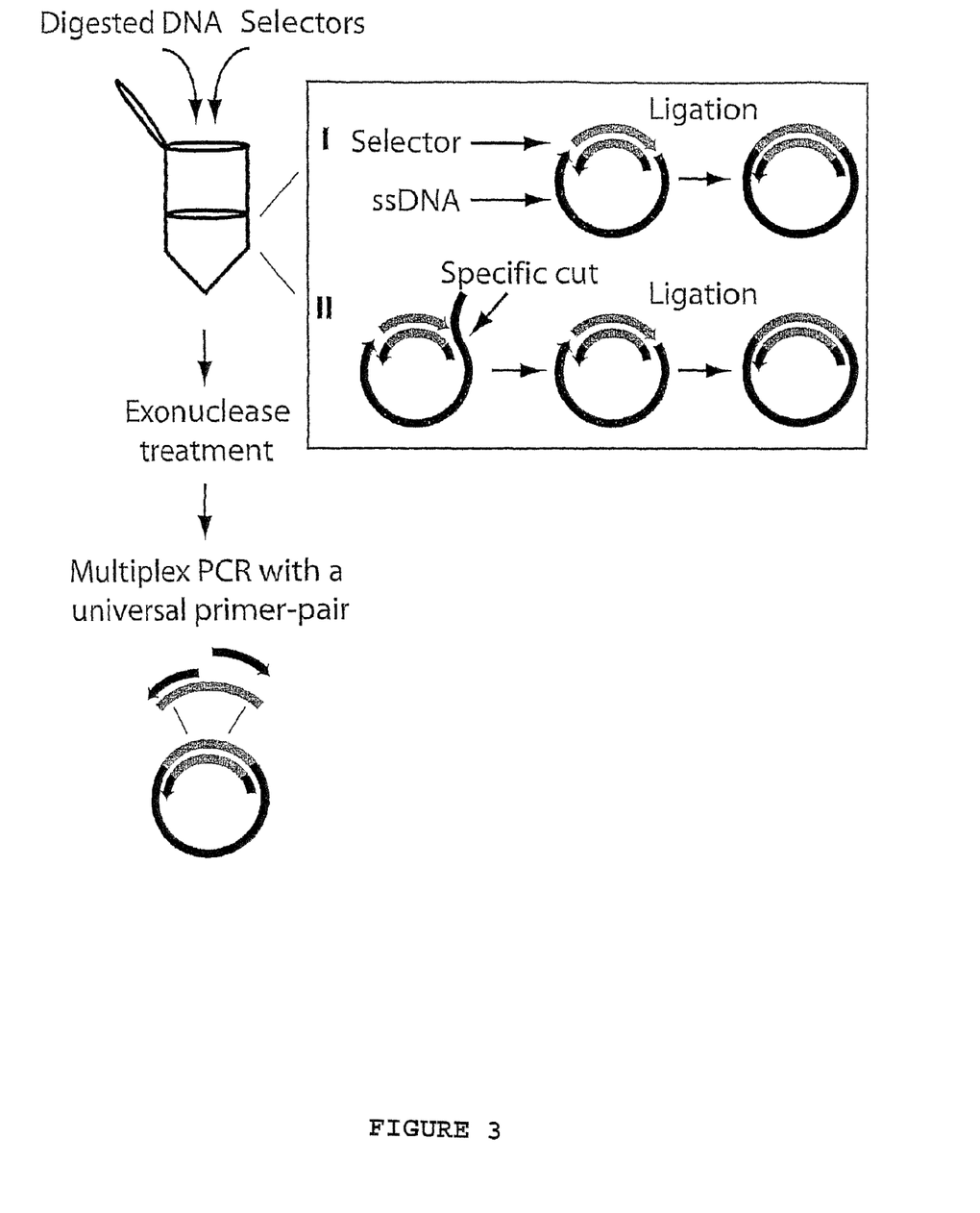
FIG. 3 illustrates an example of the scheme of the procedure where each ligation of selectors to targets can be performed in parallel and amplified in a multiplex PCR with a common primer-pair.

Example 1 describes; hybridization and ligation of ninety-six selectors to ninety-six specific target nucleic acid fragments followed by multiplex PCR using one primer-pair, according to FIG. 3. The amplified products were analyzed on microarrays and with gel electrophoresis. The sequences of the primer-pair and the two types of oligonucleotides that comprise the selectors (long and short) are described in Table 1.

Oligonucleotides and design. Ninety-six cDNA clone sequences, chosen as targets for the selector design, were blasted against the human genome sequence. For each cDNA sequence, the genomic sequence yielding the highest-scoring hit was used as target sequence. The target sequences and an additional 700 nucleotides of sequence information on both sides was downloaded and in silico restriction digested. Restriction fragments were considered suitable for selection if they contained at least 70 consecutive nucleotides complementary to the cDNA and they were between 140 and 750 nucleotides in length. Selector probes were designed against one suitable fragment for each target. The selector (long), 5'-phosphorylated vector (short), and the primer sequences are shown in Table 1.

Circularization and amplification of 96 fragments. Genomic DNA was extracted from human blood samples (Flexigene, Qiagen). Two combinations of restriction enzymes; I 10 U of Fsp I (Fermentas) and 10 U of HpyCH4 V (New England Biolabs) and II 10 U of Acu I (New England Biolabs) and 10 U of CviA II (New England Biolabs) were added to two different aliquots of 10 µg genomic DNA and 0.5 µg BSA, in a total volume of 50 µl NEBuffer 4. The restriction digestion was performed at 37° C. for 1 h. Two different circularization reactions containing 1.6 pM of each of 87 and 9 different selectors were combined with 1 µg of DNA from the restriction digestion reactions I and II, respectively. The circularization reactions was performed in PCR buffer (Invitrogen) supplemented with 10 mM $MgCl_2$, 1 mM NAD, and 3.2 nM of vector oligonucleotide, using 2.5 U Platinum Taq DNA polymerase (Invitrogen) and 5 U Ampligase (Epicentre) in a volume of 25 µl. The circularization reactions were incubated at 95° C. for 15 min, 60° C. for 20 min, followed by 50° C. over night. To enrich for circularized DNA by degrading linear strands including selectors, 10 µl of the circularization mixes (0.4 µg DNA) were then added to a 10 µl mix of 5 U Exonuclease I (New England Biolabs), 110 mM Tris-HCl pH 9.0, 3 mM $MgCl_2$, and 0.2 □g BSA and incubated for 2 h at 37° C., followed by 95° C. for 10 min. Amplification was performed using 4 µl of each exonuclease-treated circularization reaction (80 ng DNA each) added to 17 µl mix of 1×PCR buffer (Invitrogen), supplemented with 0.5 U Platinum Taq DNA polymerase (Invitrogen), 0.25 mM dNTP, 0.4 µM Cy-3 labeled forward and reverse primer, respectively, and 2 mM $MgCl_2$. Cycling was performed as follows: 95° C. for 2 min, followed by 40 cycles of 95° C. for 30 s, 55° C. for 30 s, and 72° C. for 20 s. The same procedure was performed but without ligase.

Array hybridization. cDNA arrays were obtained from the microarray core facility at Uppsala University. Arrays were prepared according to the manufactures recommendations. In brief, 7500 cDNA clones were obtained from the Sequence Verified Known Genes Collection (Research Genetics). Clone inserts were prepared using standard protocol and printed in duplicate on Ultragap slides (Corning Life Sciences) using a Cartesian Prosys 5510A (Cartesian Technologies) printer. Slides were cross-linked with 450 mJ UV-light using UV-Stratalinker 1800 (Stratagen). To verify the quality of the array, a Cy-3-labelled random 9-mer was hybridized to one of the arrays (Operon). 25 µl of amplification reaction was hybridized to a cDNA array together with 25 µl MICROMAX hybridization buffer (NEN) at 55° C., over night. The array was washed in 0.02×SSC and 0.1% Triton X-100 for two minutes, transferred to 0.1 mM $NaCl_2$ for 5 sec., and then scanned using a GenePix 4000B (Axon Instruments). Images were analyzed using GenePix Pro 5.0 (Axon Instruments). Signals were defined as positive if the ratio of fluorescence to local background exceeded a threshold value for both duplicate spots. This threshold was set so that less than 0.5% of the spots expected to be negative were scored as positive.

Figure 4A:
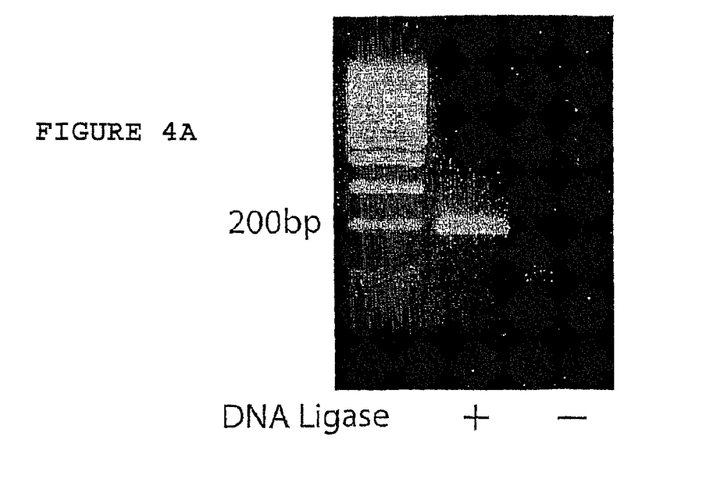
FIGS. 4A and 4B show analysis of a PCR product on a 1.5% agarose gel (FIG. 4A) and hybridization of the PCR product shown in FIG. 4A to a 7.5 k cDNA microarray (FIG. 4B).
Figure 4B:
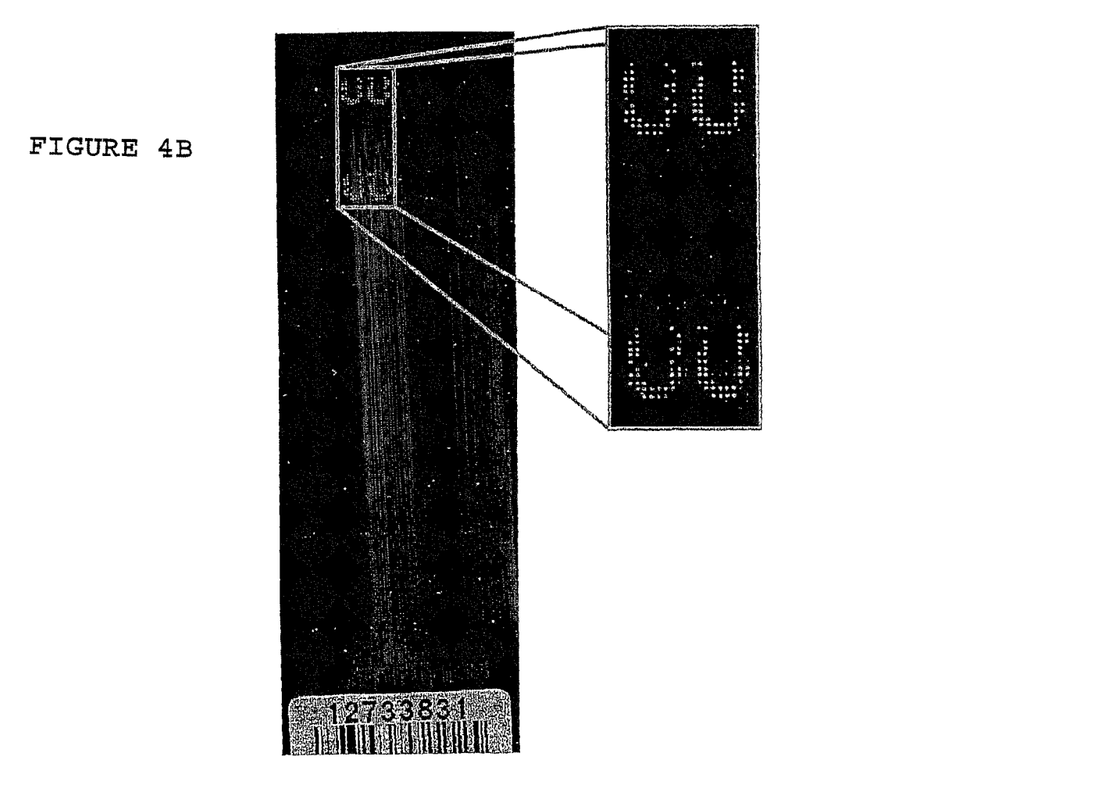

The performance of the method were assessed by selecting an unbiased set of 96 genomic fragments for amplification, and then analyzing the product by hybridization to an array of 7500 spotted human cDNA sequences. Targets in the genome that corresponded to cDNA sequences at 96 positions on the array in a pattern of UU (as in Uppsala University) were chosen. The first step in the design of the 96 selectors was to perform an in silico restriction digestions of the human genomic DNA sequence to find a combination of restriction enzymes that generated suitable fragments for all targets. Two different restriction enzyme combinations were chosen, each with two different enzymes, which formed suitable fragments for 87 and 9 targets, respectively. All selector probes were designed to generate amplification products of about 190 bp. The selector probes were purchased as a standard 96-plate synthesis and mixed in two pools, one containing 87 selector probes and the other 9 selector probes. Each pool was then combined with DNA from the appropriate digested genomic DNA sample in two separate circularization reactions. These were then subjected to exonuclease treatment, combined, and amplified in a single PCR with a universal Cy3-labeled primer pair. The PCR product was analyzed on a 1.5% agarose gel (FIG. 4A). The gel analysis showed one sharp band of approximately 190 bp, demonstrating the specificity of the amplification. The PCR product was then hybridized to the 7.5 k cDNA microarray (FIG. 4B).

Figure 5:
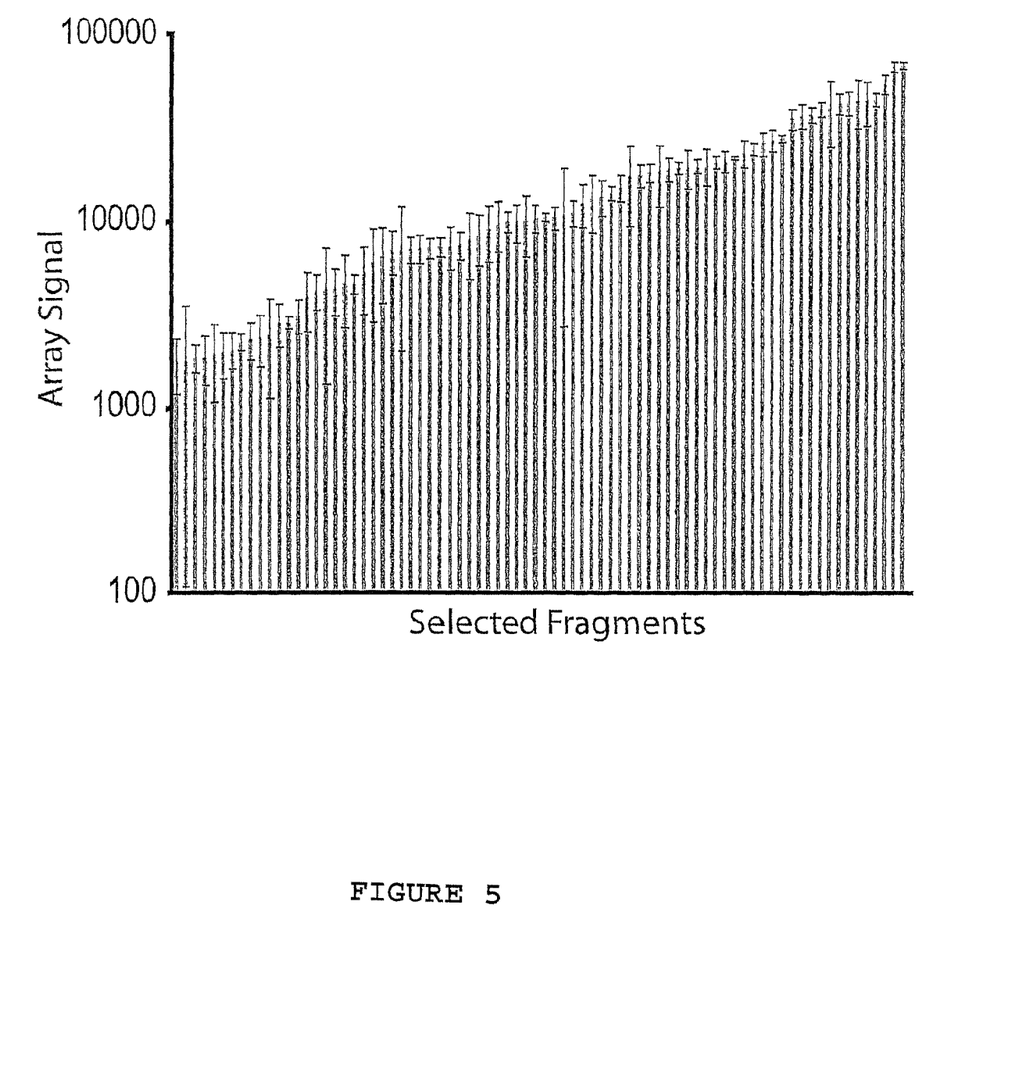
FIG. 5 is a graph of the average hybridization signal intensities of 79 positive fragments in an array.

To evaluate the reproducibility of the method the experiment was repeated using five different DNA samples. First, to verify the quality of the array, a Cy-3-labelled random 9-mer was hybridized to an array from the same spotting session. This analysis showed that 7 of the 96 selected spots lacked cDNA (not shown), limiting the number of positions that could be analyze to 89. Next, the samples were hybridized to five different slides and a threshold value was defined for each slide such that 38 of 7684 (0.5%) spots were scored positive outside the UU pattern. These spots could represent false amplification products or be due to misprinting or cross hybridizations. 79 (89%) of the selected fragments generated positive signals in at least three of five experiments, and 71 (80%) were scored positive in all five experiments. The average signal intensities of the 79 positive fragments are shown in FIG. 5. The signal intensities were reproducible with an average variation (CV) of 24%.

Adding these results together, the method confirms that it is specific and is capable to amplify a plurality of specific targets in parallel. The gel-analysis further verifies that the method only amplifies the selected sequences, since the only detectable band was 200 nucleotides long, the size of the selected targets.

TABLE 1

| SEQ ID NO: | Clone name | Selector (long) sequence 5'-3' |
|---|---|---|
| 1 | AA486321 | TAATATCTAAACAATTCTCTACGATAACGGTAGAAAGCTTTGCTAACGGTCGAGGAATACTTTTAAAAGGTAT |
| 2 | AA520978 | CTTCCTCTCATCCAAAACACGATAACGGTAGAAAGCTTTGCTAACGGTCGAGCAGCCACAGTGTTCTG |
| 3 | AA425451 | TTGTTGATATTTTCTTTTAAACGATAACGGTAGAAAGCTTTGCTAACGGTCGAGCAAAGGATGCTGGGTC |
| 4 | AA281057 | AGTGTAACAGAATATTTTTACGATAACGGTAGAAAGCTTTGCTAACGGTCGAGCAACAGGAAGAAACATCA |
| 5 | AA425767 | TCATCAGAAAAAAAAAAAAACGATAACGGTAGAAAGCTTTGCTAACGGTCGAGCAGAGGTGGAGTTACAG |
| 6 | T71606 | ACAAGGATACTTGAAACTCACGATAACGGTAGAAAGCTTGCTAACGGTCGAGCATTTGAGGCTGAGC |
| 7 | AA487521 | CTGTACTTTATCTCGGCACGATAACGGTAGAAAGCTTGCTAACGGTCGAGCAGATTTTCATCCCATTC |
| 8 | AA452840 | AAACCACAATAGTGACCCACGATAACGGTAGAAAGCTTTGCTAACGGTCGAGCAAGCTTCCACTTGGT |
| 9 | AA600189 | GTCCTGTGTGACTCAGACGATAACGGTAGAAAGCTTGCTAACGGTCGAGCACAGTAGCCACAGTT |
| 10 | AA233549 | ACAGGTCGGCCCCGTGTAGCGCACGATAACGGTAGAAAGCTTGCTAACGGTCGAGCAGGTTCTCCTGGGCGCGCACTC |
| 11 | AA663058 | AAAAATATATATCATCAAGCACGATAACGGTAGAAAGCTTTGCTAACGGTCGAGCATCAGTATTACAACTCATC |
| 12 | AA479058 | GTGGGACTCTGATCCCACGATAACGGTAGAAAGCTTTGCTAACGGTCGAGCAAAGGCCTGGGCT |
| 13 | AA664009 | ATCATATTTCTTTTATTTTGACGATAACGGTAGAAAGCTTGCTAACGGTCGAGCATCTGAAAGCAAACTTT |
| 14 | W69211 | TGTGAACCCAAAGTGTGACGATAACGGTAGAAAGCTTGCTAACGGTCGAGGAGATTCTTTACCCCCT |
| 15 | AA477400 | GCCCAAACCTTGTAGGGGCAGAAGCACGATAACGGTAGAAAGCTTTGCTAACGGTCGAGCACCGGTGGCAGGCGAGGAGGAC |
| 16 | AA446659 | TAAAATAGAAATAAGTGGTTACGATAACGGTAGAAAGCTTTGCTAACGGTCGAGCACTATGAGGAATAATTATT |
| 17 | N56693 | CAGAACTGTGGCAATGACGATAACGGTAGAAAGCTTTGCTAACGGTCGAGGCTAATACAGCACTACC |
| 18 | AA025819 | AAGAGTTTTAAACAATGAATACGATAACGGTAGAAAGCTTTGCTAACGGTCGAGCATTTCCAAACTGCCTT |
| 19 | H46254 | CTCTGGGGAAAATCCCACGATAACGGTAGAAAGCTTTGCTAACGGTCGAGGATGTAGGCCTCCTTG |
| 20 | AA444051 | GGATTTCATGAGCAGATCACGATAACGGTAGAAAGCTTTGCTAACGGTCGAGCAATGACTATTTTGTAGTAC |
| 21 | AA629189 | CCAGGCCCAAATCAAGACGATAACGGTAGAAAGCTTTGCTAACGGTCGAGGTGGGAGATGGCATTG |
| 22 | R21535 | GAAGGCCTGGGGCACGATAACGGTAGAAAGCTTGCTAACGGTCGAGGAAAAGGCAATGTCCCA |
| 23 | AA134E71 | CACGATGGGCCGCACGATAACGGTAGAAAGCTTTGCTAACGGTCGAGCACCTGCGGCTGT |
| 24 | H11003 | CTCCGGAGGATGCCACGATAACGGTAGAAAGCTTTGCTAACGGTCGAGCATTCCTTAGAAAATCTTTG |
| 25 | AA702802 | TGGGCCAGGCCCTCGCAGACGATAACGGTAGAAAGCTTTGCTAACGGTCGAGGGCTGGCCCCGGTCCCGGTTG |
| 26 | AA683085 | TCCACCTUCTGAGCACGATAACGGTAGAAAGCTTTGCTAACGGTCGAGCATTGGGATCCTTGAAC |
| 27 | N59270 | GTCAATGAGAGCCAGTACGATAACGGTAGAAAGCTTTGCTAACGGTCGAGCAATTTCTTATTTCATAAC |
| 28 | N74623_65 | GGCCCCTCCATCGGGCTGAGGACGATAACGGTAGAAAGCTTTGCTAACGGTCGAGCAGCCTCCTCCTGACCACGGACGT |
| 29 | H09730 | TCCTGTTCCCTGAACCACGATAACGGTAGAAAGCTTTGCTAACGGTCGAGCAAGTGAGGTTTCTGAG |
| 30 | AA630354 | ACATTCCAGGTCCTGTCATTGGGCGACGATAACGGTAGAAAGCTTGCTAACGGTCGAGGCGCCGGCCCCGGGGAACCT |
| 31 | AA634006 | CCGATCCAGACAGAGTACGATAACGGTAGAAAGCTTTGCTAACGGTCGAGGAGACAGAGAGGAGCA |
| 32 | AA169469 | GTATCCCAAGCAGGGAACGATAACGGTAGAAAGCTTTGCTAACGGTCGAGCATAATTTCTTTGGTCTCAT |
| 33 | N64384 | CGCCCTGAAGCCCACGATAACGGTAGAAAGCTTTGCTAACGGTCGAGCAGGCATCTCACTCC |
| 34 | H61243 | TCTCAGTGCTGGTGGACGATAACGGTAGAAAGCTTTGCTAACGGTGGAGGCCGGGCCATGC |
| 35 | AA630628 | CCTGTTGCTGCGGACGATAACGGTAGAAAGCTTTGCTAACGGTCGAGCAGGTTGACCTATTCAG |
| 36 | H80138 | CAGTGGTTTAGTAGTTTAAGACGATAACGGTAGAAAGCTTTGCTAACGGTCGAGCAGCATATTTTGTTATCTC |
| 37 | R54176 | AGTACAATCTCAACTATGTACGATAACGGTAGAAAGCTTTGCTAACGGTCGAGCATGCCAAGAAATACCC |
| 38 | AA629808 | ATGCTTACTTCAAGAAGAACGATAACGGTAGAAAGCTTGCTAACGGTCGAGGTGGCTTATTACTTGTGA |

TABLE 1-continued

| SEQ ID NO: | Clone name | Selector (long) sequence 5'-3' |
|---|---|---|
| 39 | R14080 | AGCCCTTTTAAATCAGAGACGATAACGGTAGAAAGCTTTGCTAACGGTCGAGGCTCAGCTCCCAAAA |
| 40 | T55558 | ACTGTGAGATTTTGTTTTTACGATAACGGTAGAAAGCTTTGCTAACGGTCGAGCAGAAGCTCTTTTTGAG |
| 41 | AA705382 | AGGAAACACCGGAACCACGATAACGGTAGAAAGCTTTGCTAACGGTCGAGCATGGCATATGTCTTCT |
| 42 | AA759046 | ATACCCGGGAGCCTGCTTGGACCTCACGATAACGGTAGAAAGCTTTGCTAACGGTCGAGGCCCTGTGGGCAGGGGTTGGAAACT |
| 43 | AA775423 | TGCCTGGGACTGTTGCCTTGTACCGACGATAACGGTAGAAAGCTTTGCTAACGGTCGAGCAGTCAACGGAACGGTGCCGCTGA |
| 44 | AA846573 | GTCAGCGCCCGACACGATAACGGTAGAAAGCTTTGCTAACGGTCGAGGATAAAAAGTTAAAAAAAA |
| 45 | AA725641 | GCAGTTGTTGTAGCAGACGATAACGGTAGAAAGCTTTGCTAACGGTCGAGCAAAGCAATGAAAGACATA |
| 46 | N59790 | GGACGGCCAAACTGACGATAACGGTAGAAAGCTTTGCTAACGGTCGAGGGGAAAGCAACACAGG |
| 47 | N74524_65 | CTCAATAAATAAATTAATTGTTGTCACGATAACGGTAGAAAGCTTTGCTAACGGTCGAGCATCCTCCCTGCCTCACTCCCCTCA |
| 48 | AA775091 | CGTTTTTGTTTTGTTTTGTACGATAACGGTAGAAAGCTTTGCTAACGGTCGAGCAACCCTTTCCCCAG |
| 49 | N31587 | AGGGTGTGAAGGCTGACGATAACGGTAGAAAGCTTTGCTAACGGTCGAGCAGACGACAGCGG |
| 50 | AA775874 | GACGGGCCAGCTGACGATAACGGTAGAAAGCTTTGCTAACGGTCGAGCAGCACCGTCCTGC |
| 51 | AA862434 | CGAGACTTCTCTTTCTTACGATAACGGTAGAAAGCTTTGCTAACGGTCGAGCAGCTATTGCTCTGG |
| 52 | AA129135 | GCTTCATGGCCTGGACGATAACGGTAGAAAGGTTTGCTAACGGTCGAGCACCCTGTACAGTTGC |
| 53 | AA485376 | CAGGAAGGACCGGAACGATAACGGTAGAAAGCTTTGCTAACGGTCGAGCAGAGCTGCTGGAG |
| 54 | AA262074 | CTCCCTTGGCTGGCACGATAACGGTAGAAAGCTTTGCTAACGGTCGAGCAGCTCAGCCTGGT |
| 55 | AA465378 | GGAGGGGGCGTGCGGGGCACGATAACGGTAGAAAGCTTTGCTAACGGTCGAGGGCTCCGGCTGGCGTTGAGCA |
| 56 | H15539 | AGCTGCCCATTTTGTGACGATAACGGTAGAAAGCTTTGCTAACGGTCGAGCAGCAGGGGATGGG |
| 57 | AA258001 | CCCACAAGGCTGGCGGTGCCTCCACGATAACGGTAGAAAGCTTTGCTAACGGTCGAGCACGGCTCCTCCACCTCCCTCCCC |
| 58 | AA281784 | GACCAGCACTCTGTGACGATAACGGTAGAAAGCTTTGCTAACGGTCGAGCAAAGCCACAGCGT |
| 59 | AA459244 | TGGCTTCTTGCCTGACGATAACGGTAGAAAGCTTTGCTAACGGTCGAGCATCATCTTATAANTGANTA |
| 60 | AA520979 | ACCATATATTCTATATTTTACGATAACGGTAGAAAGCTTTGCTAACGGTCGAGCAATTGGCTAAGTTGTCA |
| 61 | R55188 | TAAATGATTCTGTAGAGGCCCCGTGACGATAACGGTAGAAAGCTTTGCTAACGGTCGAGCAAATTTTAGGGTCCTGAGCCAAGT |
| 62 | R45413 | ATCACCTGAGGTCAGGACGATAACGGTAGAAAGCTTGCTAACGGTCGAGGGAAGTCAGTGGAGC |
| 63 | AA464711 | TCTATCCCAAACTAAGCTACGATAACGGTAGAAAGCTTTGCTAACGGTCGAGCAAATTCTCAAGCCGC |
| 64 | R97308 | TACAAAAACCATTAXACAGAACGATAACGGTAGAAAGTTGCTAACGGTCGAGCAGTAAATGGCGTACAC |
| 65 | H05655 | CACTCTCTACATGTTATTTAACGATAACGGTAGAAAGCTTTGCTAACGGTCGAGGAGGGTGGGAGATGG |
| 66 | AA463642 | CAGAGTTGTGATCCAAGACGATAACGGTAGAAAGCTTTGCTAACGGTCGAGGCCCCTTGCTGTAAC |
| 67 | AA455145 | CCTCCAGCAGCCCAGCCTGTTCACACGATAACGGTAGAAAGCTTTGCTAACGGTCGAGGTAAGGTGCCCAAGACCACATAGCA |
| 68 | W65461 | TTTTTATAGTGTAAAATAAAACGATAACGGTAGAAAGCTTGCTAACGGTCGAGCAACGTGGTACTACTTTT |
| 69 | H23255 | TCTTTTAACTTTGGTTTAAAACGATAACGGTAGAAAGCTTTGCTAACGGTCGAGCAGAATCGAAACTTCTC |
| 70 | R45255 | TAAATAGTTATATTACGATCACGATAACGGTAGAAAGCTTTGCTAACGGTCGAGGACTAAAAGATTGAGAAGTT |
| 71 | H07899 | CCATAATAGAAAATCGATGAACGATAACGGTAGAAAGCTTTGCTAACGGTCGAGCAGATGAGCTCCAGTC |
| 72 | H82891 | TGCGCTGCTGACCACGATAACGGTAGAAAGCTTTGCTAACGGTCGAGCACTTTGGTGACATTGTT |
| 73 | R43015 | CTTAGTTAGCCATTGATGACGATAACGGTAGAAAGCTTTGCTAACGGTCGAGGTAGCTGAGATTTAATGG |
| 74 | H22445 | TGTATATACTGTATAATATGACGATAACGGTAGAAAGCTTTGCTAACGGTCGAGCAATTTGTTGAAAGGGAAC |

TABLE 1-continued

| SEQ ID NO: | Clone name | Selector (long) sequence 5'-3' |
|---|---|---|
| 75 | AA496691 | GGGAAACTCTGACTTGGACGATAACGGTAGAAAGCTTTGCTAACGGTCGAGGGGCGACGGAG |
| 76 | N69204 | ACAGAAATAGAGATGCTATACGATAACGGTAGAAAGCTTTGCTAACGGTCGAGCATCTTGGTGATATTTTAA |
| 77 | H65034 | CAATGGTAGTGGTGGTAACGATAACGGTAGAAAGCTTTGCTAACGGTCGAGCAATTAAGCTCAGCAAG |
| 78 | R01211 | GGAAGCCTCTAATCCTACGATAACGGTAGAAAGCTTTGCTAACGGTCGAGCATTGTTCACTTACATGTC |
| 79 | AA045588 | TATTATATAAGTGACTGAATACGATAACGGTAGAAAGCTTTGCTAACGGTCGAGCAGCAATATCTATAATGACT |
| 80 | R37937 | GGACTTTACTATTCATAATGACGATAACGGTAGAAAGCTTTGCTAACGGTCGAGGTAAATCACAGTGGTTCAA |
| 81 | H84982 | CCACCAGCGACTCCACGATAACGGTAGAAAGCTTTGCTAACGGTCGAGCAGGAATGGCATCACC |
| 82 | H50323 | GGAGCCTGGATAAGCACGATAACGGTAGAAAGCTTTGCTAACGGTCGAGCAGCAGTGGGGGTG |
| 83 | H45618 | ACTTTGGGAGGCCGACGATAACGGTAGAAAGCTTTGCTAACGGTCGAGCAGTCTGTAAGAAACACA |
| 84 | AA041400 | GTGCTAACCACACAATAAACGATAACGGTAGAAAGCTTTGCTAACGGTCGAGCATTTACTTTAAAAGAAAAA |
| 85 | W31391 | CTACTGGTTGGCCCTAACGATAACGGTAGAAAGCTTTGCTAACGGTCGAGCAGTGTCCGGAGGC |
| 86 | H16824 | GGCAGGGCGTCCAACGATAACGGTAGAAAGCTTTGCTAACGGTCGAGCATTATTAGGCAAAGATCC |
| 87 | AA085619 | CATTACAAATGTCTCAGCACGATAACGGTAGAAAGCTTTGCTAACGGTCGAGCAAATGCCTTCTTGCT |
| 88 | AA446108 | AATGACCCCCAGAGCACGATAACGGTAGAAAGCTTTGCTAACGGTCGAGGTCTCCGCAGAATTCC |
| 89 | AA486850 | CAGTTGCTGAAAGAGCACGATAACGGTAGAAAGCTTTGCTAACGGTCGAGGCTGAGTCTGCACAG |
| 90 | R40790 | TGACCCGGAGTGAACACGATAACGGTAGAAAGCTTTGCTAACGGTCGAGGAATGTGGAGGAAATTTTC |
| 91 | AA292536 | TGCACATTTGAAATAAACCACGATAACGGTAGAAAGCTTTGCTAACGGTCGAGGGATTGGTCTGAGGGG |
| 92 | N71782 | TTCAGCCTCTGATGTCACGATAACGGTAGAAAGCTTTGCTAACGGTCGAGAGGGAATAAACACAACAC |
| 93 | AA664180 | CACCCCTCACTGGTCCACTGGCTTGACGATAACGGTAGAAAGCTTGCTAACGGTCGAGGAGGGAGGGGCCCAAAGCCCTTGTG |
| 94 | AA774044 | ATCCTGGAGACCCTGACGATAACGGTAGAAAGCTTTGCTAACGGTCGAGTTACTTATTTCCCCTTCTT |
| 95 | R39227 | AGAGTCGCTCCACAACGATAACGGTAGAAAGCTTTGCTAACGGTCGAGCGCTTCAAGGAAACC |
| 96 | AA464152 | AAAATAAAAAAGGACAAAAGACGATAACGGTAGAAAGCTTTGCTAACGGTCGAGGTGTAAGGCACTGCC |
| 97 | Vector (short) | 5'P ctcgaccgttagcaaagctttctaccgttatcgt 3' |
| 98 | Primer forw | agctttgctaacggtcgag |
| 99 | Primer rev | Agctttgtaccgttatcgt |

The invention claimed is:

1. A method of amplifying a plurality of target sequences in a nucleic acid sample, comprising the steps:
  (a) fragmenting the nucleic acid sample into fragments wherein each fragment that includes a target sequence has at least one defined end sequence,
  (b) denaturing the nucleic acid sample, if the nucleic acid sample is double-stranded, to produce single-stranded fragments
  (c) bringing the single-stranded fragments in contact with a plurality of (i) one or (ii) two double-stranded selector constructs, wherein:
  in (i) said selector construct comprises a long oligonucleotide and a short oligonucleotide hybridized thereto such that the long oligonucleotide contains two protruding end sequences complementary to the defined end sequences, or complementary to one defined end sequence and one defined internal sequence, of the target-containing nucleic acid fragments, and wherein both oligonucleotides contain at least one primer motif such that the selector construct contains a primer-pair motif; and
  in (ii) said two selector constructs each comprise a long oligonucleotide and a short oligonucleotide hybridized thereto such that the long oligonucleotides each contain one protruding end sequence, said protruding end sequences being complementary to each defined end sequence of the target-containing nucleic acid fragment, and wherein the long oligonucleotides and the short oligonucleotides contain at least one primer motif such that the selector constructs contain a primer-pair motif, (d) allowing the protruding end sequences of the selectors to hybridized with the fragments,
(e) joining the selectors and fragments by ligation, and
(f) amplifying the selected target sequences in parallel using a primer-pair specific for the primer-pair motif common to at least a subset of the selectors, which subset has a unique primer-pair motif,
wherein, if in (c)(i) a protruding end sequence of the selector construct is complementary to a defined internal sequence of the target-containing nucleic acid fragment, after hybridization (d) the protruding end of the target-containing nucleic acid fragment is cleaved by an endonucleolytic enzyme at the hybridization duplex position before ligation (e).

2. The method according to claim 1, wherein all selectors comprise a common primer-pair motif.

3. The method according to claim 2, wherein the endonucleolytic enzyme is a FLAP endonucleolytic enzyme.

4. The method according to claim 3, wherein the fragmentation of the nucleic acid sample is accomplished using at least one restriction enzyme.

5. The method according to claim 4, wherein the amplification is performed by PCR.

6. The method according to claim 1, wherein the endonucleolytic enzyme is a FLAP endonucleolytic enzyme.

7. The method according to claim 1, wherein the fragmentation of the nucleic acid sample is accomplished using at least one restriction enzyme.

8. The method according to claim 2, wherein the fragmentation of the nucleic acid sample is accomplished using at least one restriction enzyme.

9. The method according to claim 2, wherein the amplification is performed by PCR.

10. The method according to claim 1, wherein the amplification is performed by PCR.

11. The method according to claim 3, wherein the amplification is performed by PCR.

12. The method according to claim 1 (c)(i), wherein remaining linear DNA fragments are removed by enzymatic digestion after ligation of the selectors and fragments to form circular molecules.

13. The method according to claim 1, further comprising an analysis of the generated amplification products using gel electrophoresis, hybridization arrays, sequencing by synthesis, liquid chromatography and/or mass spectrometry.

14. The method according to claim 1, further comprising the step of analyzing genetic variability, identifying microorganisms, analyzing expression, sequencing a genome and/or measuring DNA copy number.

* * * * *